(12) United States Patent
Caparso et al.

(10) Patent No.: US 7,979,141 B2
(45) Date of Patent: *Jul. 12, 2011

(54) TRANSVASCULAR RESHAPING LEAD SYSTEM

(75) Inventors: Anthony V. Caparso, San Jose, CA (US); Julia Moffitt, Iowa City, IA (US); Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/564,416

(22) Filed: Sep. 22, 2009

(65) Prior Publication Data

US 2010/0016927 A1    Jan. 21, 2010

Related U.S. Application Data

(63) Continuation of application No. 11/130,022, filed on May 16, 2005, now Pat. No. 7,617,003.

(51) Int. Cl.
*A61N 1/05* (2006.01)

(52) U.S. Cl. .................... 607/116; 607/117; 607/118

(58) Field of Classification Search .................. 607/117, 607/116, 119

See application file for complete search history.

(56) References Cited

U.S. PATENT DOCUMENTS

| | | | |
|---|---|---|---|
| 3,692,027 A | 9/1972 | Ellinwood, Jr. | |
| 4,003,379 A | 1/1977 | Ellinwood, Jr. | |
| 4,082,097 A | 4/1978 | Mann et al. | |
| 4,146,029 A | 3/1979 | Ellinwood, Jr. | |
| 4,217,910 A | 8/1980 | Khalil | |
| 4,522,208 A | 6/1985 | Buffet | |
| 4,871,351 A | 10/1989 | Feingold | |
| 4,944,299 A | 7/1990 | Silvian | |
| 4,987,897 A | 1/1991 | Funke | |
| 5,042,497 A | 8/1991 | Shapland | |
| 5,052,388 A | 10/1991 | Sivula et al. | |
| 5,111,815 A | 5/1992 | Mower | |

(Continued)

FOREIGN PATENT DOCUMENTS

EP    0467695 A2    1/1992

(Continued)

OTHER PUBLICATIONS

"U.S. Appl. No. 11/103,245, Non-Final Office Action mailed Jan. 11, 2008", 9 pgs.

(Continued)

*Primary Examiner* — Carl H. Layno
*Assistant Examiner* — Jon-Eric C. Morales
(74) *Attorney, Agent, or Firm* — Faegre & Benson LLP

(57) ABSTRACT

A system for selective activation of a nerve trunk using a transvascular reshaping lead is provided. One aspect of this disclosure relates to a system for spreading nerve bundles in a nerve trunk. The system includes a lead adapted to be chronically implanted in a blood vessel proximate a nerve trunk, and having an expandable portion adapted to be expanded to reshape the blood vessel to an elongated shape and to reshape the nerve trunk into an elongated shape to spread nerve bundles of the nerve trunk. The system also includes a plurality of electrodes and an implantable device coupled to the lead, where an electrical signal is delivered from the implanted medical device to one of the plurality of electrodes to transvascularly deliver neural stimulation from the electrode to at least one of the nerve bundles of the nerve trunk. Other aspects and embodiments are provided herein.

20 Claims, 8 Drawing Sheets

U.S. PATENT DOCUMENTS

| | | | |
|---|---|---|---|
| 5,199,428 A | 4/1993 | Obel et al. | |
| 5,203,326 A | 4/1993 | Collins | |
| 5,300,875 A | 4/1994 | Tuttle | |
| 5,318,592 A | 6/1994 | Schaldach | |
| 5,324,316 A | 6/1994 | Schulman et al. | |
| 5,330,507 A | 7/1994 | Schwartz | |
| 5,342,408 A | 8/1994 | deCoriolis et al. | |
| 5,354,318 A | 10/1994 | Taepke | |
| 5,436,548 A | 7/1995 | Thomas | |
| 5,496,360 A | 3/1996 | Hoffmann et al. | |
| 5,501,703 A | 3/1996 | Holsheimer et al. | |
| 5,522,854 A | 6/1996 | Ideker et al. | |
| 5,531,779 A | 7/1996 | Dahl et al. | |
| 5,540,730 A | 7/1996 | Terry, Jr. et al. | |
| 5,551,953 A | 9/1996 | Lattin et al. | |
| 5,562,711 A | 10/1996 | Yerich et al. | |
| 5,562,713 A | 10/1996 | Silvian | |
| 5,578,061 A | 11/1996 | Stroetmann et al. | |
| 5,662,689 A | 9/1997 | Elsberry et al. | |
| 5,700,282 A | 12/1997 | Zabara | |
| 5,707,400 A | 1/1998 | Terry, Jr. et al. | |
| 5,775,338 A | 7/1998 | Hastings | |
| 5,800,498 A | 9/1998 | Obino et al. | |
| 5,814,089 A | 9/1998 | Stokes et al. | |
| 5,843,142 A | 12/1998 | Sultan | |
| 5,846,218 A | 12/1998 | Brisken et al. | |
| 5,916,239 A | 6/1999 | Geddes et al. | |
| 5,972,029 A | 10/1999 | Fuisz | |
| 6,006,134 A | 12/1999 | Hill et al. | |
| 6,073,048 A | 6/2000 | Kieval et al. | |
| 6,115,636 A | 9/2000 | Ryan | |
| 6,117,085 A | 9/2000 | Picatti et al. | |
| 6,140,740 A | 10/2000 | Porat et al. | |
| 6,141,588 A | 10/2000 | Cox et al. | |
| 6,164,284 A | 12/2000 | Schulman et al. | |
| 6,205,361 B1 | 3/2001 | Kuzma et al. | |
| 6,206,914 B1 | 3/2001 | Soykan et al. | |
| 6,213,942 B1 | 4/2001 | Flach et al. | |
| 6,231,516 B1 | 5/2001 | Keilman et al. | |
| 6,237,398 B1 | 5/2001 | Porat et al. | |
| 6,240,316 B1 | 5/2001 | Richmond et al. | |
| 6,292,695 B1 | 9/2001 | Webster, Jr. et al. | |
| 6,292,703 B1 | 9/2001 | Meier et al. | |
| 6,358,202 B1 | 3/2002 | Arent | |
| 6,445,953 B1 | 9/2002 | Bulkes et al. | |
| 6,453,195 B1 | 9/2002 | Thompson | |
| 6,456,866 B1 | 9/2002 | Tyler et al. | |
| 6,511,500 B1 | 1/2003 | Rahme | |
| 6,518,245 B1 | 2/2003 | Anderson et al. | |
| 6,519,488 B2 | 2/2003 | KenKnight et al. | |
| 6,522,926 B1 | 2/2003 | Kieval et al. | |
| 6,564,096 B2 | 5/2003 | Mest | |
| 6,584,362 B1 | 6/2003 | Scheiner et al. | |
| 6,622,041 B2 | 9/2003 | Terry, Jr. et al. | |
| 6,645,145 B1 | 11/2003 | Dreschel et al. | |
| 6,656,960 B2 | 12/2003 | Puskas | |
| 6,778,854 B2 | 8/2004 | Puskas | |
| 6,788,970 B1 | 9/2004 | Park et al. | |
| 6,798,716 B1 | 9/2004 | Charych | |
| 6,802,811 B1 | 10/2004 | Slepian | |
| 6,804,561 B2 | 10/2004 | Stover | |
| 6,805,998 B2 | 10/2004 | Jenson et al. | |
| RE38,705 E | 2/2005 | Hill et al. | |
| 6,934,583 B2 | 8/2005 | Weinberg et al. | |
| 7,294,334 B1 | 11/2007 | Michal et al. | |
| 7,499,748 B2 | 3/2009 | Moffitt et al. | |
| 7,617,003 B2* | 11/2009 | Caparso et al. | 607/116 |
| 2002/0004670 A1 | 1/2002 | Florio et al. | |
| 2002/0026221 A1 | 2/2002 | Hill et al. | |
| 2002/0026222 A1 | 2/2002 | Schauerte et al. | |
| 2002/0042637 A1 | 4/2002 | Stover | |
| 2002/0072776 A1 | 6/2002 | Osorio et al. | |
| 2002/0107557 A1 | 8/2002 | Edell et al. | |
| 2002/0161410 A1 | 10/2002 | Kramer et al. | |
| 2002/0165586 A1 | 11/2002 | Hill et al. | |
| 2002/0183237 A1 | 12/2002 | Puskas | |
| 2002/0183793 A1 | 12/2002 | Struble et al. | |
| 2002/0198570 A1 | 12/2002 | Puskas | |
| 2002/0198571 A1 | 12/2002 | Puskas | |
| 2003/0023279 A1 | 1/2003 | Spinelli et al. | |
| 2003/0045909 A1 | 3/2003 | Gross et al. | |
| 2003/0060848 A1 | 3/2003 | Kieval et al. | |
| 2003/0060858 A1 | 3/2003 | Kieval et al. | |
| 2003/0074039 A1 | 4/2003 | Puskas | |
| 2003/0078623 A1 | 4/2003 | Weinberg et al. | |
| 2003/0078629 A1 | 4/2003 | Chen | |
| 2003/0100924 A1 | 5/2003 | Foreman et al. | |
| 2003/0114905 A1 | 6/2003 | Kuzma | |
| 2003/0132731 A1 | 7/2003 | Chung | |
| 2003/0158584 A1 | 8/2003 | Cates et al. | |
| 2003/0195578 A1 | 10/2003 | Perron et al. | |
| 2003/0199958 A1 | 10/2003 | Zhang et al. | |
| 2003/0212440 A1 | 11/2003 | Boveja | |
| 2004/0030362 A1 | 2/2004 | Hill et al. | |
| 2004/0059383 A1 | 3/2004 | Puskas | |
| 2004/0122477 A1 | 6/2004 | Whitehurst et al. | |
| 2004/0186531 A1 | 9/2004 | Jahns et al. | |
| 2004/0220621 A1 | 11/2004 | Zhou et al. | |
| 2005/0065553 A1 | 3/2005 | Ben Ezra et al. | |
| 2005/0085864 A1 | 4/2005 | Schulman et al. | |
| 2005/0096705 A1 | 5/2005 | Pastore et al. | |
| 2005/0143412 A1 | 6/2005 | Puskas | |
| 2005/0143779 A1 | 6/2005 | Libbus | |
| 2005/0143785 A1 | 6/2005 | Libbus | |
| 2005/0143787 A1 | 6/2005 | Boveja et al. | |
| 2005/0149126 A1 | 7/2005 | Libbus | |
| 2005/0149127 A1 | 7/2005 | Libbus | |
| 2005/0149128 A1 | 7/2005 | Heil et al. | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149155 A1 | 7/2005 | Scheiner et al. | |
| 2005/0149156 A1* | 7/2005 | Libbus et al. | 607/119 |
| 2005/0187584 A1 | 8/2005 | Denker et al. | |
| 2005/0197675 A1 | 9/2005 | David et al. | |
| 2006/0079945 A1 | 4/2006 | Libbus | |
| 2006/0229677 A1 | 10/2006 | Moffitt et al. | |
| 2006/0259107 A1 | 11/2006 | Caparso et al. | |
| 2007/0093875 A1 | 4/2007 | Chavan et al. | |
| 2009/0149900 A1 | 6/2009 | Moffitt et al. | |

FOREIGN PATENT DOCUMENTS

| | | |
|---|---|---|
| EP | 0547734 A2 | 6/1993 |
| EP | 1304135 A2 | 4/2003 |
| EP | 1486232 A2 | 12/2004 |
| EP | 1541193 A1 | 6/2005 |
| WO | WO-94/07564 A2 | 4/1994 |
| WO | WO-97/33513 A1 | 9/1997 |
| WO | WO-99/65561 A1 | 12/1999 |
| WO | WO-03/076008 A1 | 9/2003 |
| WO | WO-03/082080 A2 | 10/2003 |
| WO | WO-03/105658 A2 | 12/2003 |
| WO | WO-2005/042091 A1 | 5/2005 |
| WO | WO-2005/063332 A1 | 7/2005 |
| WO | WO-2005/065771 A1 | 7/2005 |
| WO | WO-2006/110338 A1 | 10/2006 |
| WO | WO-2007/050657 A1 | 5/2007 |

OTHER PUBLICATIONS

"U.S. Appl. No. 11/103,245, Notice of Allowance mailed Oct. 20, 2008", 4 pgs.

"U.S. Appl. No. 11/103,245, Response filed Jul. 11, 2008 to Non-Final Office Action mailed Jan. 11, 2008", 14 pgs.

"U.S. Appl. No. 11/103,245, Response filed Oct. 17, 2007 to Restriction Requirement mailed Sep. 18, 2007", 7 pgs.

"U.S. Appl. No. 11/103,245, Restriction Requirement mailed Sep. 18, 2007", 6 pgs.

"U.S. Appl. No. 11/130,022, Non-Final Office Action mailed Jan. 28, 2009", 6 pgs.

"U.S. Appl. No. 11/130,022, Non-Final Office Action mailed May 15, 2008", 10 pgs.

"U.S. Appl. No. 11/130,022, Notice of Allowance mailed Jul. 21, 2009", 6 pgs.

"U.S. Appl. No. 11/130,022, Response filed Apr. 28, 2009 to Non Final Office Action mailed Jan. 28, 2009", 11 pgs.

"U.S. Appl. No. 11/130,022, Response filed Aug. 15, 2008 to Non-Final Office Action mailed May 15, 2008", 18 pgs.

"U.S. Appl. No. 11/256,907, Restriction Requirement mailed Mar. 21, 2008", 11 pgs.

"U.S. Appl. No. 11/256,907, Response filed Nov. 7, 2008 to Non-Final Office Action mailed Jul. 8, 2008", 12 pgs.

"U.S. Appl. No. 11/256,907, Final Office Action mailed Mar. 27, 2009", 9 pgs.

"U.S. Appl. No. 11/256,907, Notice of Allowance mailed Jul. 1, 2009", 5 pgs.

"U.S. Appl. No. 11/256,907, Response filed May 27, 2009 to Final Office Action mailed Mar. 27, 2009", 10 pgs.

"U.S. Appl. No. 11/256,907, Non-Final Office Action mailed Jul. 8, 2008", 7 pgs.

"European Application Serial No. 06836504.8, Office Action mailed Oct. 9, 2008", 5pgs.

"International Application Serial No. PCT/US2006/011882, International Search Report and Written Opinion mailed Aug. 2, 2006", 13 pgs.

"International Application Serial No. PCT/US2006/041569, International Search Report and Written Opinion mailed Mar. 7, 2007", 14 pgs.

"Structural Remodeling of Cardiac Myocytes in Hypertrophy and Progression to Failure; and, On Atrial Remodeling and Drug Treatment of Atrial Fibrillation", *In Cardiac Remodeling and Failure, in Section II. Remodeling and Heart Failure*, Singal, et al., editors: Kluwer Academic Publishers, (2003), 183-193; 319-330.

Caparso, A., "System for Selective Activation of a Nerve Trunk Using a Transvascular Reshaping Lead", U.S. Appl. No. 11/130,022, filed May 16, 2005, 33 pgs.

Carr, W. N., "Integrated Pressure Sensor With Remote Power Source and Remote Readout", *The 8th International Conference on Solid-State Sensors and Actuators and Eurosensors IX (TRANDUCERS '95), Digest of Technical Papers*, (1995), 624-627.

Dunlap, M. E., et al., "Mechanisms of altered vagal control in heart failure: influence of muscarinic receptors and acetylcholinesterase activity", *Am J Phsyiol Heart Circ Physiol.*, 285(4), (Oct. 2003), H1632-H1640.

Grassi, G., et al., "Sympathetic Response to Ventricular Extrasystolic Beats in Hypertension and Heart Failure", *Hypertension*, 39(4), (2002), 886-891.

Jacobsson, F., et al., "The effect of transcutaneous electric nerve stimulation in patients with therapy-resistant hypertension", *Journal of Human Hyptertension*, 14(12), (2000), 795-798.

Janes, R. D., "Anatomy of Human Extrinsic Cardiac Nerves and Ganglia.", *Am J Cardiol.*, 57(4), (1986), 299-309.

Leventhal, D. K., et al., "Subfascicle Stimulation Selectivity with the Flat Interface Nerve Electrode", *Annals of Biomedical Engineering*, 31(6), (2003), 643-652.

Li, M., "Vagal Nerve Stimulation Markedly Improves Long-Term Survival After Cronic Hart Filure in Rts", *Circulation*, 109(1), (2004), 120-124.

Libbus, I., "Integrated Lead for Applying Cardiac Resynchronization Therapy and Neural Stimulation Therapy", U.S. Appl. No. 11/077,970, filed Mar. 11, 2005, 67 pgs.

Libbus, I., et al., "Method and Apparatus for Synchronizing Neural Simulation to Cardiac Cycles", U.S. Appl. No. 11/099,141, filed Apr. 5, 2005, 36 pgs.

Libbus, I., et al., "System and Method for Closed-Loop Neural Stimulation", U.S. Appl. No. 10/992,319, filed Nov. 18, 2004, 50 pgs.

Libbus, I., "Cardiac Rhythm Management Device With Neural Sensor", U.S. Appl. No. 10/992,320, filed Nov. 18, 2004, 65 pgs.

Libbus, I., "Implantable Device for Treating Epilepsy and Cardiac Rhythm Disorders", U.S. Appl. No. 11/312,178, filed Dec. 21, 2005, 39 pgs.

Libbus, I., "Neural Stimulation With Avoidance of Inappropriate Stimulation" U.S. Appl. No. 11/000,249, filed Nov. 30, 2004, 45 pgs.

Libbus, I., "Stimulator for Auricular Branch of Vagus Nerve", U.S. Appl. No. 11/005,703, filed Dec. 7, 2004, 35 pgs.

Libbus, Imad, "System to Provide Myocardial and Neural Stimulation", U.S. Appl. No. 11/087,935, filed Mar. 23, 2005, 52 pgs.

Moffitt, Julia, "Combined Neural Stimulation and Cardiac Resynchronization Therapy", U.S. Appl. No. 11/078,460, filed Mar. 11, 2005, 35 pgs.

Moffitt, Julia, "Transvascular Neural Stimulation Device", U.S. Appl. No. 11/103,245, filed Apr. 11, 2005, 33 pgs.

Nolan, J., et al., "Prospective Study of Heart Rate Variability and Mortality in Chronic Heart Failure: Results of the United Kingdom Heart Failure Evaluation and Assessment of Risk Trial (UK-Heart).", *Circulation*, 98(15), (1998), 1510-1516.

Schauerte, P, "Catheter Stimulation of Cardiac Parasympathetic Nerves in Humans: a Novel Approach to the Cardiac Autonomic Nervous System", *Circulation*, 104(20), (2001), 2430-2435.

Schauerte, P., et al., "Ventricular Rate Control During Atrial Fibrillation by Cardiac Parasympathetic Nerve Stimulation: A Transvenous Approach", *Journal of the American College of Cardiology*, 34(7), (1999), 2043-2050.

Schauerte, P. N., et al., "Transvenous Parasympathetic Cardiac Nerve Stimulation: An Approach for Stable Sinus Rate Control", *Journal of Cardiovascular Electrophysiology*, 10(11), (1999), 1517-1524.

Schauerte, P., et al., "Transvenous Parasympathetic Nerve Stimulation in the Inferior Vena Cava and Atrioventricular Conduction", *Journal of Cardiovascular Electrophysiology*, 11(1), (2000), 64-69.

Scherlag, B. J., et al., "Endovascular stimulation within the left pulmonary artery to induce slowing of heart rate and paroxysmal atrial fibrillation.", *Cardiovascular Research*, 54(2), (2002), 470-475.

Scherlag, M. A., et al., "Endovascular Neural Stimulation Via a Novel Basket Electrode Catheter: Comparison of Electrode Configurations", *Journal of Interventional Cardiac Electrophysiology*, 4(1), (2000), 219-224.

Sigurdsson, A., et al., "The Role of Neurohormonal Activation in Chronic Heart Failure and Postmyocardial Infarction", *American Heart Journal*, 132(1, Part 2), (1996), 229-234.

Thompson, G. W., "Bradycardia Induced by Intravascular Versus Direct Stimulation of the Vagus Nerve", *Annals of Thoracic Surgery*, 65(3), (1998), 637-642.

Tyler, D J, et al., "Chronic Response of the Rat Sciatic Nerve to the Flat Interface Nerve Electrode", *Annals of Biomedical Engineering*, 31(6), (2003), 633-642.

Vanoli, E., et al., "Vagal Stimulation and Prevention of Sudden Death in Conscious Dogs With a Healed Myocardial Infarction", *Circulation Research*, 68(5), (1991), 1471-1481.

Ziaie, B., et al., "A Single-Channel Implantable Microstimulator for Functional Neuromuscular Stimulation", *IEEE Transactions on Biomedical Engineering*, 44, (1997), 909-920.

* cited by examiner

TRANSVASCULAR RESHAPING LEAD SYSTEM

CROSS REFERENCE TO RELATED APPLICATION

This application is a continuation of U.S. application Ser. No. 11/130,022, filed May 16, 2005, now U.S. Pat. No. 7,617,003 which is hereby incorporated by reference in its entirety.

TECHNICAL FIELD

This disclosure relates generally to implantable medical devices and, more particularly, to systems for selective activation of a nerve trunk using a transvascular reshaping lead.

BACKGROUND

The autonomic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. A change in autonomic balance is reflected in changes in heart rate, heart rhythm, cardiac contractility, remodeling, inflammation and blood pressure. Changes in autonomic balance can also be seen in other physiological changes, such as changes in abdominal pain, appetite, stamina, emotions, personality, muscle tone, sleep, and allergies, for example.

Reduced autonomic balance (increase in sympathetic and decrease in parasympathetic cardiac tone) during heart failure has been shown to be associated with left ventricular dysfunction and increased mortality. Research also indicates that increasing parasympathetic tone and reducing sympathetic tone may protect the myocardium from further remodeling and predisposition to fatal arrhythmias following myocardial infarction. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult.

Selective activation has been defined as the ability to activate or stimulate single axons or small groups of axons (nerve bundles) within a common nerve trunk without stimulating other portions of the nerve. Selective activation is achievable through complex practices such as current steering, use of inter-neural electrodes, and use of selective geometries.

SUMMARY

The above-mentioned problems and others not expressly discussed herein are addressed by the present subject matter and will be understood by reading and studying this specification.

Disclosed herein, among other things, is a method for spreading nerve bundles in a nerve trunk. The method includes expanding an expandable portion of a lead, adapted to be chronically implanted in a blood vessel proximate a nerve trunk, to reshape the blood vessel to an elongated shape and to reshape the nerve trunk into an elongated shape to spread nerve bundles of the nerve trunk. The method also includes delivering an electrical signal from an implanted medical device to an electrode positioned at the expandable portion of the lead to transvascularly deliver neural stimulation from the electrode to at least one of the nerve bundles of the nerve trunk. According to various embodiments, delivering an electrical signal includes delivering neural stimulation to selectively activate the nerve trunk. According to various embodiments, expanding an expandable portion of a lead to reshape the nerve trunk to an elongated shape includes bringing neural fibers of interest closer to the one of the plurality of electrodes, reducing a threshold bias for stimulating the nerve trunk. According to further embodiments, expanding an expandable portion of a lead to reshape the nerve trunk to an elongated shape includes increasing available area for electrical contact placement.

One aspect of this disclosure relates to an electronic lead for spreading nerve bundles in a nerve trunk. According to one embodiment, the electronic lead includes a proximal portion adapted to connect to an implantable medical device and an expandable portion adapted to be chronically implanted in a blood vessel proximate a nerve trunk, the expandable portion further adapted to be expanded to reshape the blood vessel to an elongated shape and to reshape the nerve trunk into an elongated shape to spread nerve bundles of the nerve trunk. The electronic lead further includes a plurality of electrodes along the expandable portion of the lead, where an electrical signal is delivered from the implanted medical device to one of the plurality of electrodes to transvascularly deliver neural stimulation from the electrode to at least one of the nerve bundles of the nerve trunk.

One aspect of this disclosure relates to a system for spreading nerve bundles in a nerve trunk. According to one embodiment, the system includes a lead having a proximal portion and an expandable portion, the expandable portion adapted to be chronically implanted in a blood vessel proximate a nerve trunk, and the expandable portion further adapted to be expanded to reshape the blood vessel to an elongated shape and to reshape the nerve trunk into an elongated shape to spread nerve bundles of the nerve trunk. The system also includes a plurality of electrodes along the expandable portion of the lead and an implantable device coupled to the proximal portion of the lead. According to one embodiment, the implantable device includes a controller circuit to communicate with a neural stimulator, a telemetry circuit to communicate with the controller circuit and an external module, a memory circuit to communicate with the controller circuit, and computer-readable instructions embedded in the memory circuit. According to one embodiment, the computer-readable instructions are operable on by the controller to deliver an electrical signal to one of the plurality of electrodes to transvascularly deliver neural stimulation from the electrode to at least one of the nerve bundles of the nerve trunk.

Another aspect of this disclosure relates to a system for selective activation of a nerve trunk. According to one embodiment, the system includes means for generating a neural stimulation signal. The system also includes means for providing the neural stimulation signal to a nerve bundle, including means for chronically implanting a lead within a blood vessel proximate a nerve trunk, wherein the lead is adapted to expand and reshape the blood vessel and nerve trunk to spread the nerve bundles of the nerve trunk. According to various embodiments, the means for providing the neural stimulation includes a means for delivering neural stimulation to selectively activate the nerve trunk.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

Figure 1:
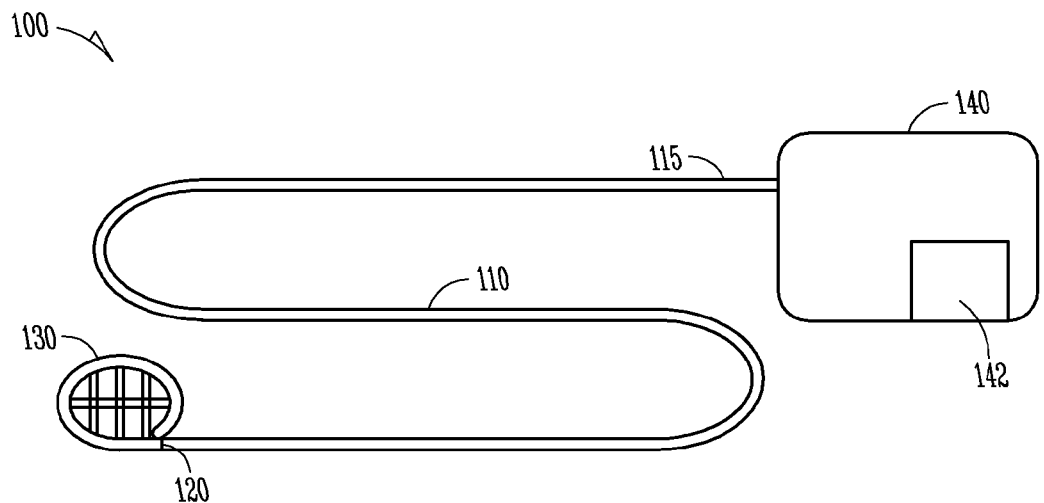
FIG. 1 illustrates a lead and an implantable medical device (IMD), according to one embodiment.

The following detailed description refers to the accompanying drawings which show, by way of illustration, specific aspects and embodiments in which the present invention may be practiced. The various embodiments are not necessarily mutually exclusive, as aspects of one embodiment can be combined with aspects of another embodiment. These embodiments are described in sufficient detail to enable those skilled in the art to practice the invention. Other embodiments may be utilized and structural, logical, and electrical changes may be made without departing from the scope of the present invention.

Neural stimulation has been the subject of a number of studies and has been proposed for several therapies. The autonomic system controls physiological activities of the body and the imbalance of autonomic tone is related to many diseases and conditions. Vagus nerve stimulation has been proposed to treat sleep disorders, gastrointestinal motility, eating disorders, obesity, anorexia, gastrointestinal tract disorders, hypertension, coma, and epilepsy. Direct electrical stimulation of parasympathetic nerves can induce a reduction of sympathetic nerve activity and reduce blood pressure by decreasing vascular resistance. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

Transvascular stimulation of a vagus nerve trunk is used in a number of therapies. In an example, vagal nerve stimulation simultaneously increases parasympathetic tone and decreases sympathetic myocardial tone. In an example, a vagus nerve trunk is transvascularly stimulated following cardiac ischemic insult. Increased sympathetic nervous activity following ischemia often results in increased exposure of the myocardium to epinephrine and norepinephrine. These catecholamines activate intracellular pathways within the myocytes, which lead to myocardial death and fibrosis. This effect is inhibited by stimulation of the parasympathetic nerves, such as vagus nerves. In an example, transvascular vagal stimulation from within the SVC lowers heart rate, overall blood pressure, and left ventricular pressure. Stimulation of the vagal cardiac nerves following myocardial infarction, or in heart failure patients, can be beneficial in preventing further remodeling and arrhythmogenesis.

In other examples, transvascular neural stimulation is used to treat other conditions such as hypertrophic cardiomyopathy (HCM) or neurogenic hypertension, where an increase parasympathetic cardiac tone and reduction in sympathetic cardiac tone is desired. In another example, a bradycardia condition is treated by transvascularly stimulating a sympathetic nerve trunk. In another example, the ionotropic state of the heart is increased by transvascularly stimulating a sympathetic nerve trunk. Transvascular sympathetic stimulation can also be used to treat orthostatic hypotension.

Selective activation (or selective stimulation) of nerve bundles within a nerve trunk has several benefits, including: allowing the ability to control one of a group of end organs; avoiding synergistic affects; decreasing the necessary stimulus amplitudes; and allowing coordinated movements or actions. Reshaping the nerve trunk improves access to nerve bundles for selective activation.

Transvascular Reshaping Lead

The lead apparatus disclosed herein is sometimes referred to as a transvascular reshaping lead, as the lead both delivers transvascular therapy and reshapes the surrounding vessel and adjacent nerve trunk. This provides for more reliable and efficient chronic selective activation, provides a greater amount of surface area for placement of stimulating electrodes, and allows for monophasic stimulation using lower amplitude and shorter pulse widths. In addition, the disclosed lead provides for a less invasive means for providing these benefits than using an intra-neural electrode or cuff electrode. As shown in the figures and discussed below, the disclosed lead reshapes the blood vessel by expanding asymmetrically along the radial axis of the vessel against the inner wall of the vessel, and reshapes the nerve trunk into an elongated shape as the vessel expands against the adjacent trunk. In this manner, the reshaping lead includes a transvascular prosthetic device.

The reshaping lead brings the nerve of interest into closer contact with the lead placed within the vessel, but it also serves as a stabilizing mechanism for the lead. By reshaping the vessel, the lead inherently also acts as its own fixation mechanism. In addition, the lead apparatus disclosed herein has the ability to sense an electrical signal from the nerve to be stimulated.

The lead can be used to stimulate or sense the nerve of interest when a vein, artery, or other vessel is running in close proximity to the nerve bundle. In one embodiment, the vessel and nerve bundle are within a common sheath.

FIG. 1 illustrates a lead and an implantable medical device (IMD), according to one embodiment. Lead 100 includes a flexible lead body 110 extending from a proximal end 115 to a distal end 120. An expandable portion 130 is proximate the distal end 120 of lead body 110. As will be discussed below, expandable portion 130 is adapted to spread nerve bundles in a nerve trunk.

Lead 100 is coupled to an implantable medical device (IMD) 140, or pulse generator. Lead 100 includes conductors, such as coiled conductors that electrically couple pulse generator 140 to expandable portion 130. Accordingly, implantable medical device 140 can deliver a stimulation signal to via the proximal portion 130. The lead further includes outer insulation to insulate the conductor. The system can include a unipolar system with the case acting as an electrode or a bipolar system with a pulse between two distally located electrodes.

In one embodiment, implantable medical device 140 includes hardware, circuitry and software to perform neural stimulation functions, and includes controller circuitry 142. The controller circuitry 142 is capable of being implemented using hardware, software, and combinations of hardware and software. For example, according to various embodiments, the controller circuitry 142 includes a processor to perform instructions embedded in a memory to perform functions associated with neural stimulation, including selective activation. The lead is adapted to be placed intravenously in a blood vessel. In one embodiment, the lead is placed intravenously through the inferior jugular vein. In another embodiment, the lead is placed intravenously through the subclavian vein. The lead is adapted to be placed in other vessels, as will be discussed below with respect to FIGS. 8A-8E.

Figure 2:
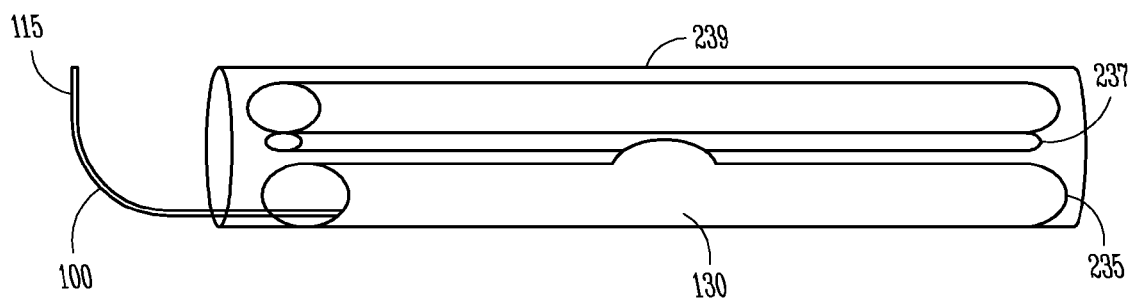
FIG. 2 illustrates an apparatus for spreading nerve bundles in a nerve trunk, according to one embodiment.

FIG. 2 illustrates an apparatus for spreading nerve bundles in a nerve trunk, according to one embodiment. An electronic lead 100 is shown for spreading nerve bundles in a nerve trunk. According to one embodiment, the electronic lead 100 includes a proximal portion 115 adapted to connect to an implantable medical device and an expandable portion 130 adapted to be chronically implanted in a blood vessel 235 proximate a nerve trunk 237, the expandable portion further adapted to be expanded to asymmetrically expand the blood vessel against the nerve trunk to reshape the nerve trunk and spread nerve bundles of the nerve trunk. In one embodiment, the vessel and nerve bundle are within a common sheath 239.

Figure 3A:
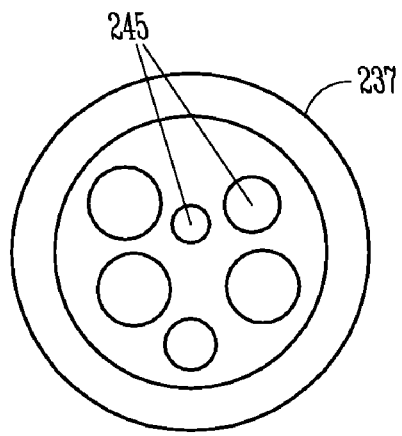
FIG. 3A illustrates an example of nerve bundles in a nerve trunk, according to one embodiment.

FIG. 3A illustrates an example of nerve bundles 245 in a nerve trunk 237, according to one embodiment. The depicted nerve trunk 237 is cylindrical and contains a plurality of cylindrical nerve bundles 245, or groups of axons. The overlapping of the bundles 245 creates an obstacle to selective transvascular activation of specific nerve bundles without affecting neighboring bundles.

Figure 3B:
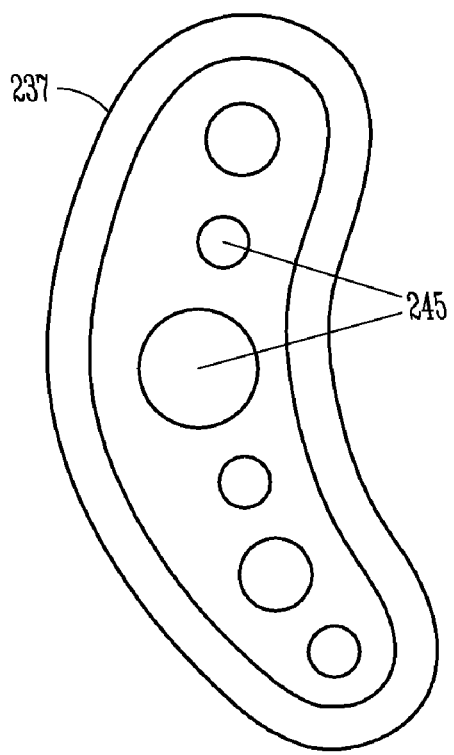
FIG. 3B illustrates spreading nerve bundles in a nerve trunk, according to one embodiment.

FIG. 3B illustrates spreading nerve bundles in a nerve trunk, according to one embodiment. The nerve trunk of FIG. 3B is shown after the present system has reshaped the nerve trunk into an elongated shape by asymmetrically expanding the adjacent blood vessel to "flatten out" or spread the trunk 237. The reshaped trunk 237 contains a spread of nerve bundles 245. The depicted embodiment shows the reorganized bundles 245 in a row. Those of skill in the art will appreciate that specific nerve bundles (or fascicles) can more easily be targeted for selective activation in this geometry, as neural fibers of interest are brought closer to the electrode containing lead. Selective activation can then be achieved using simple monophasic low current amplitude stimuli, or using field steering techniques. In addition, selective activation can be achieved chronically in this setting, and an increased area for electrical contact placement is provided.

An embodiment of the electronic lead, like the one shown at 100 in FIG. 2, includes a biased, expandable portion. In this embodiment, a plurality of discrete electrodes is placed around the outer circumference of the expandable portion. According to various embodiments, an electrical signal is delivered from the implanted medical device to one of the plurality of electrodes to transvascularly deliver neural stimulation from the electrode to at least one of the nerve bundles of the nerve trunk. In other embodiments, the entire biased oval portion can be an exposed electrode. Oval biased expandable portion is dimensioned to expand the distal end to asymmetrically expand a blood vessel against the nerve trunk to reshape the nerve trunk and spread nerve bundles of the nerve trunk. Other embodiments can use other angles as needed. In an embodiment, the expandable portion includes an electroactive polymer, or shape memory polymer, that is pre-molded in a desired configuration and collapsible to be delivered through a catheter.

Besides an oval design, the electronic lead can have other configurations to reshape vessels and nerve trunks. In one embodiment, the lead is a stent design to reshape the vessel and has an area of high contact density to increase selective activation techniques. The stent can be deployed by a balloon that expands only in one radial direction to produce a flattened oval shape. In one embodiment, the stent can be made of nitinol to retain its shape once deployed and after any trauma that may occur to the vessel after deployment. In another embodiment, the lead is a bias lead that will also have capability to reshape the vessel and have many electrical contacts for stimulation. A mechanically expandable lead using a screw located at the proximal end is included in a further embodiment. In this embodiment, turning the screw expands a series of spines to asymmetrically expand the lead. An example of this embodiment includes three spines on opposite sides of the lead body including a middle spine and two shorter adjacent spines, and turning the screw shortens the lead and expands the middle spine outward and expands the two adjacent spines that straddle the middle spine outward to a lesser extent than the middle spine.

System for Delivering Selective Transvascular Stimulation

Figure 4:
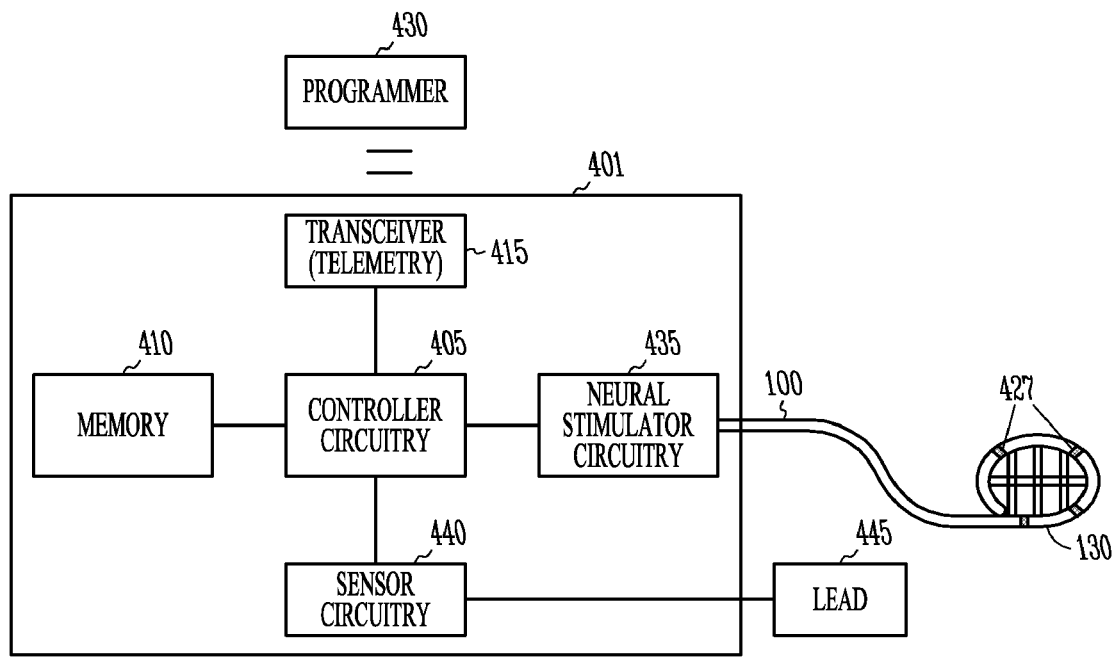
FIG. 4 is a schematic illustration of an implantable system for delivering selective transvascular stimulation, according to one embodiment.

FIG. 4 is a schematic illustration of an implantable system for delivering selective transvascular stimulation, according to one embodiment. The system includes an implantable device 401, an electrical lead 100 coupled to the implantable device 401, and an expandable portion 130 of the lead containing stimulation electrodes 427. The implantable device includes a controller circuit 405, a memory circuit 410, a telemetry circuit 415, and a neural stimulation circuit 435. The controller circuit 405 is operable on instructions stored in the memory circuit to deliver an electrical stimulation therapy. Therapy is delivered by the neural stimulation circuit 435 through the lead 100 and the electrodes 427. The telemetry circuit 415 allows communication with an external programmer 430. The illustrated system also includes optional sensor circuitry 440 that is coupled to a lead 445. In various embodiments, the electrical lead 100 having the expandable portion can function as a sensor lead. The controller circuit 405 processes sensor data from the sensor circuitry and delivers a therapy responsive to the sensor data.

Figure 5:
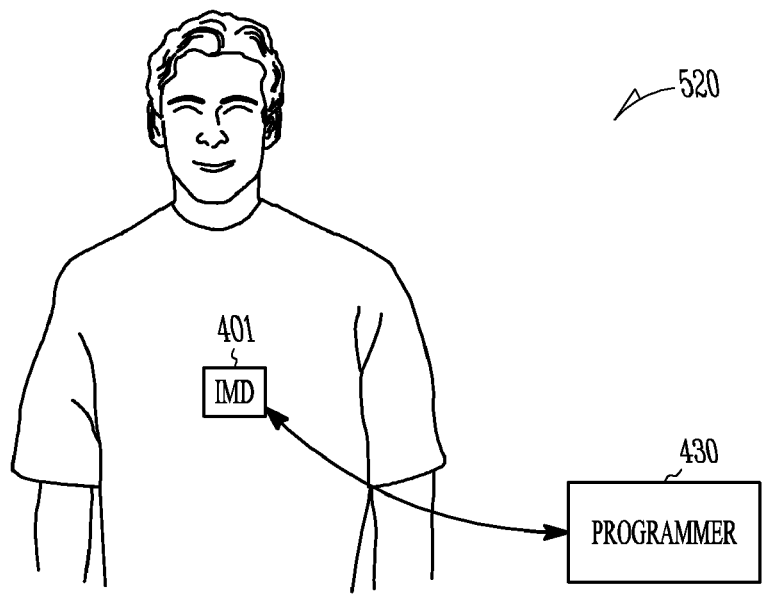
FIG. 5 illustrates a system including an implantable medical device (IMD) and a programmer, according to one embodiment.

FIG. 5 illustrates a system 520 including an implantable medical device (IMD) 401 and a programmer 430, according to one embodiment. Various embodiments of the IMD 401 include neural stimulator functions only, and various embodiments include a combination of neural stimulation and cardiac rhythm management functions. The programmer 430 and the IMD 401 are capable of wirelessly communicating data and instructions. In various embodiments, for example, the programmer 430 and IMD 401 use telemetry coils to wirelessly communicate data and instructions. Thus, the programmer can be used to adjust the programmed therapy provided by the IMD 401, and the IMD can report device data (such as battery and lead resistance) and therapy data (such as sense and stimulation data) to the programmer using radio telemetry, for example. According to various embodiments, the IMD 401 selectively stimulates nerve bundles spread using the method disclosed in FIG. 7 below. According to various embodiments, the IMD 401 includes a sensor to sense ANS activity. Such a sensor can be used to perform feedback in a closed loop control system. For example, various embodiments sense surrogate parameters, such as respiration and blood pressure, indicative of ANS activity. According to various embodiments, the IMD further includes cardiac stimulation capabilities, such as pacing and defibrillating capabilities in addition to the capabilities to stimulate nerve bundles and/or sense ANS activity.

Figure 6:
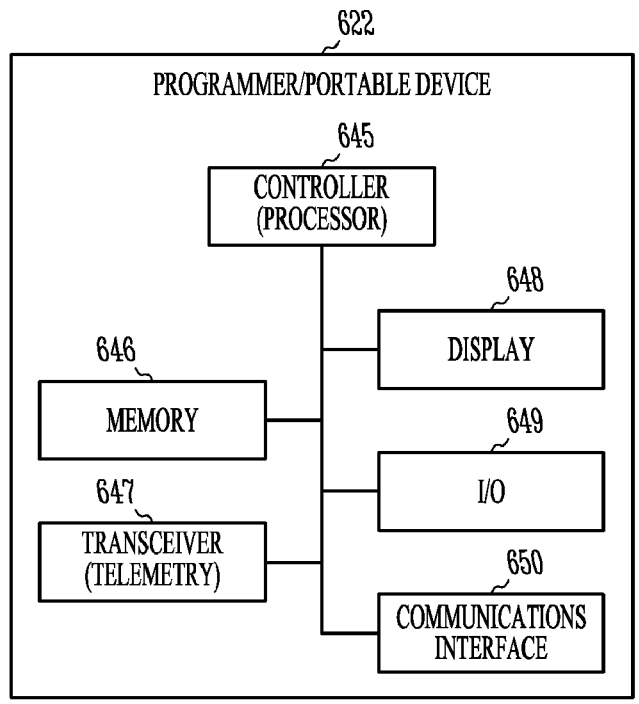
FIG. 6 illustrates a programmer such as illustrated in the system of FIG. 5 or other external device to communicate with the implantable medical device(s), according to one embodiment.

FIG. 6 illustrates a portable device 622, such as the programmer 430 illustrated in the system of FIG. 5 or other external device to communicate with the implantable medical device(s), according to one embodiment. An example of another external device includes Personal Digital Assistants (PDAs) or personal laptop and desktop computers in an Advanced Patient Management (APM) system. The illustrated device 622 includes controller circuitry 645 and a memory 646. The controller circuitry 645 is capable of being implemented using hardware, software, and combinations of hardware and software. For example, according to various embodiments, the controller circuitry 645 includes a processor to perform instructions embedded in the memory 646 to perform a number of functions, including communicating data and/or programming instructions to the implantable devices. The illustrated device 622 further includes a transceiver 647 and associated circuitry for use to communicate with an implantable device. Various embodiments have wireless communication capabilities. For example, various embodiments of the transceiver 647 and associated circuitry include a telemetry coil for use to wirelessly communicate with an implantable device. The illustrated device 622 further includes a display 648, input/output (I/O) devices 649 such as a keyboard or mouse/pointer, and a communications interface 650 for use to communicate with other devices, such as over a communication network.

Method for Spreading Nerve Bundles

Figure 7:
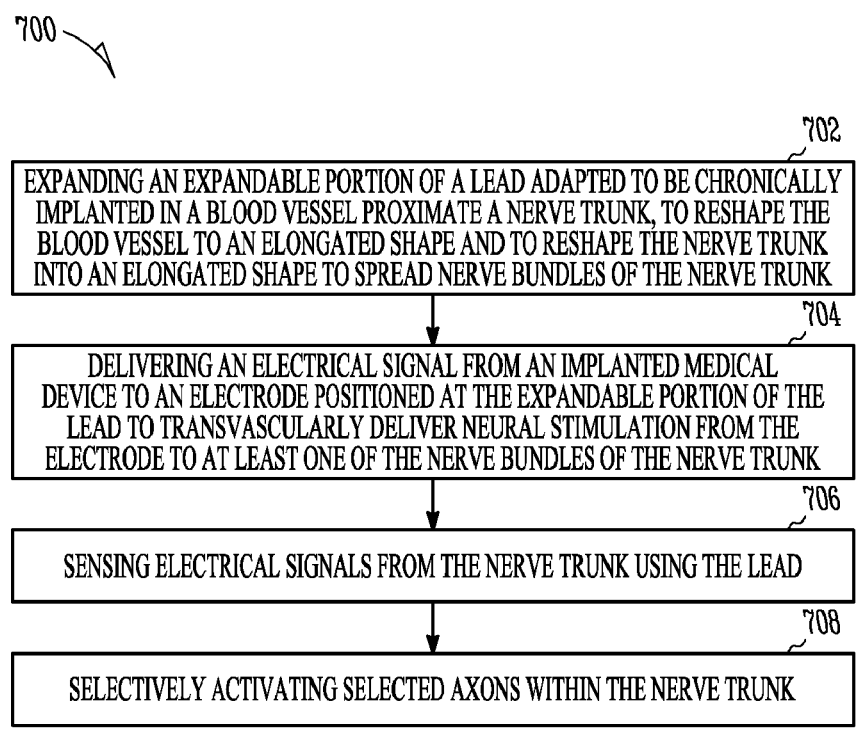
FIG. 7 illustrates a flow diagram of a method for spreading nerve bundles in a nerve trunk, according to one embodiment.

FIG. 7 illustrates a flow diagram of a method for spreading nerve bundles in a nerve trunk, according to one embodiment. The method 700 includes expanding an expandable portion of a lead, adapted to be chronically implanted in a blood vessel proximate a nerve trunk, to reshape the blood vessel to an elongated shape and to reshape the nerve trunk into an elongated shape to spread nerve bundles of the nerve trunk, at 702. The method also includes delivering an electrical signal from an implanted medical device to an electrode positioned at the expandable portion of the lead to transvascularly deliver neural stimulation from the electrode to at least one of the nerve bundles of the nerve trunk, at 704. In one embodiment, the vessel and nerve bundle are within a common sheath.

According to an embodiment, the method includes sensing electrical signals from the nerve targeted for stimulation, at 706. According to various embodiments, delivering an electrical signal includes delivering neural stimulation to selectively activate small amounts of axons within the nerve trunk, at 708. Not all embodiments of the disclosed method use all steps depicted in FIG. 7.

According to various embodiments, expanding an expandable portion of a lead to reshape the nerve trunk to an elongated shape includes bringing neural fibers of interest closer to the one of the plurality of electrodes, reducing a threshold bias for stimulating the nerve trunk. According to further embodiments, expanding an expandable portion of a lead to reshape the nerve trunk to an elongated shape includes increasing available area for electrical contact placement. The disclosed method takes advantage of cervical anatomy to reshape the geometry of a nerve to position neural tissue where simple stimulation protocols can be used to selectively activate small sub-populations of fibers, according to various embodiments. In addition, in an embodiment the lead selectively activates afferent or efferent axons within the nerve bundle.

Lead Placement Targets

Figure 8A:
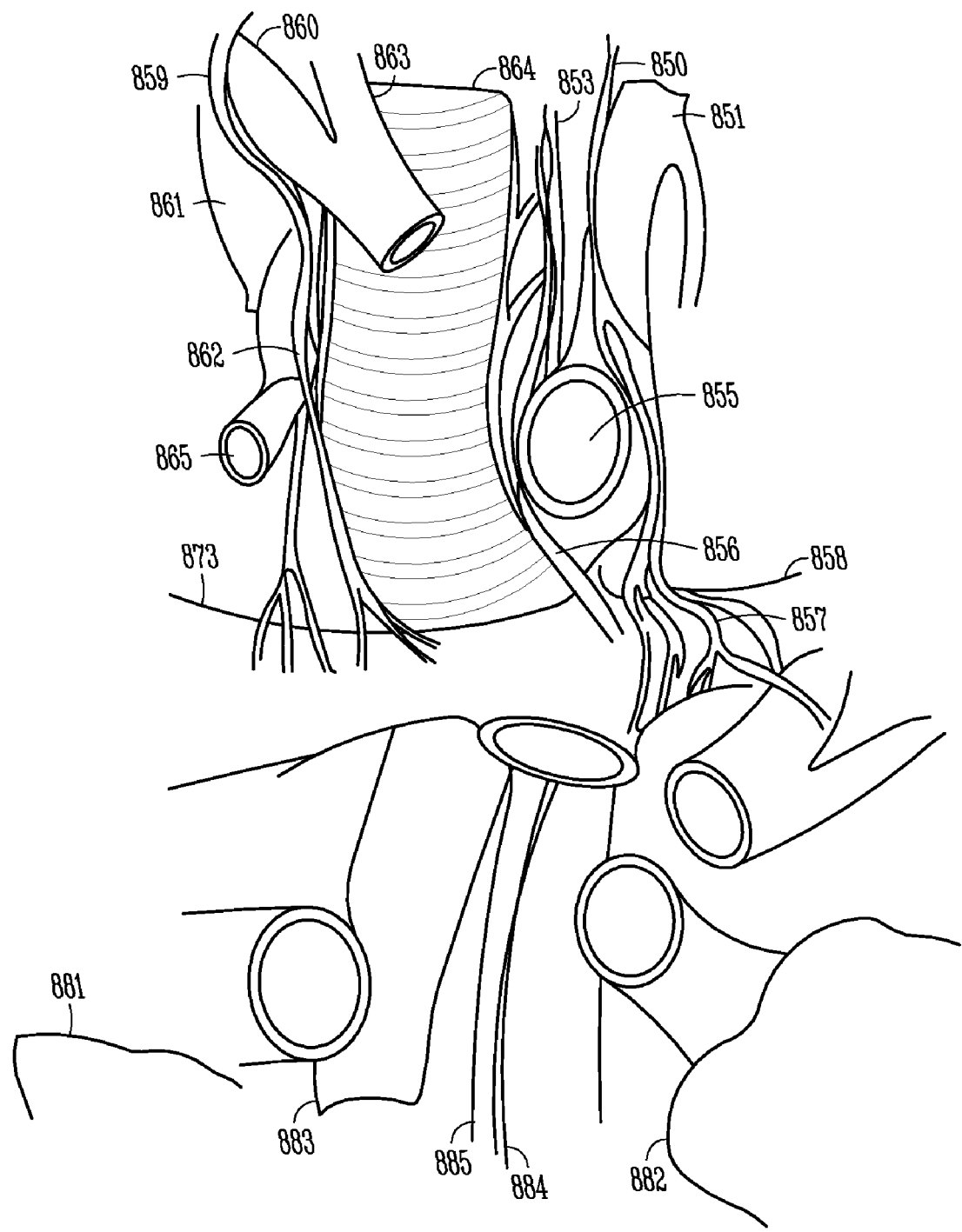
FIGS. 8A and 8B are illustrations of blood vessels and nerve trunks used by the present system, according to various embodiments.
Figure 8B:
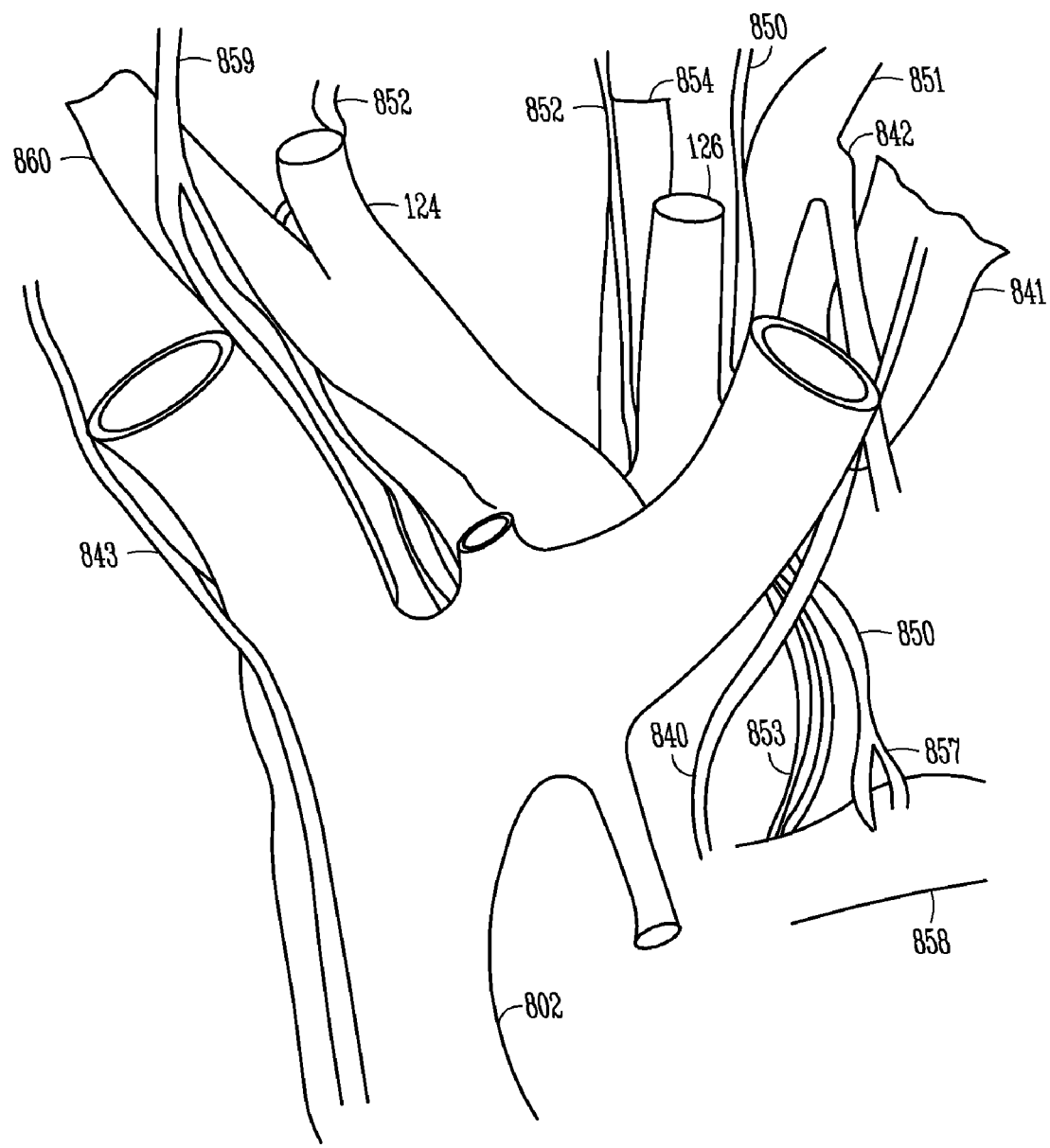

FIGS. 8A and 8B are illustrations of blood vessels and nerve trunks used by the present system, according to various embodiments. FIG. 8A shows left vagus nerve 850 extending next to a subclavian artery 851. Various nerves extend around the arch of the aorta 855. Vagus nerve 850 also extends past the ligamentum arteriosum 856. The anterior pulmonary plexus 857 crosses the left pulmonary artery 858. Right vagus nerve 859 extends past a subclavian artery 860 and the cupola of pleura 861. Cardiac nerves 862 extend past the brachiocephalic trunk 863 near the trachea 864. Cardiac nerves 862 also extend past the arch of an azygos vein 865 to the right pulmonary artery 873. In the lower portion of FIG. 8A appear the right lung 881, left lung 882, esophagus 883, a lower portion 884 of the left vagus nerve 850, and a lower portion 885 of the aorta. FIG. 8B shows a left phrenic nerve 840 extending past a cupola of pleura 841, an internal thoracic artery 842, and left pulmonary artery 858 Vagus nerve 850, recurrent laryngeal nerves 852, cardiac nerves 853, and the anterior pulmonary plexus 857 extend near the left pulmonary artery 858 and ligamentum arteriosum. A lead with an expandable portion containing electrodes, such as a stent, is chronically implantable in the blood vessels shown in FIG. 8A or 8B to selectively transvascularly stimulate a nerve or nerve trunk that extends on or near the blood vessel. In one example, the vagus nerve is transvascularly stimulated from the azygos vein 865 or internal jugular vein.

Figure 8D:
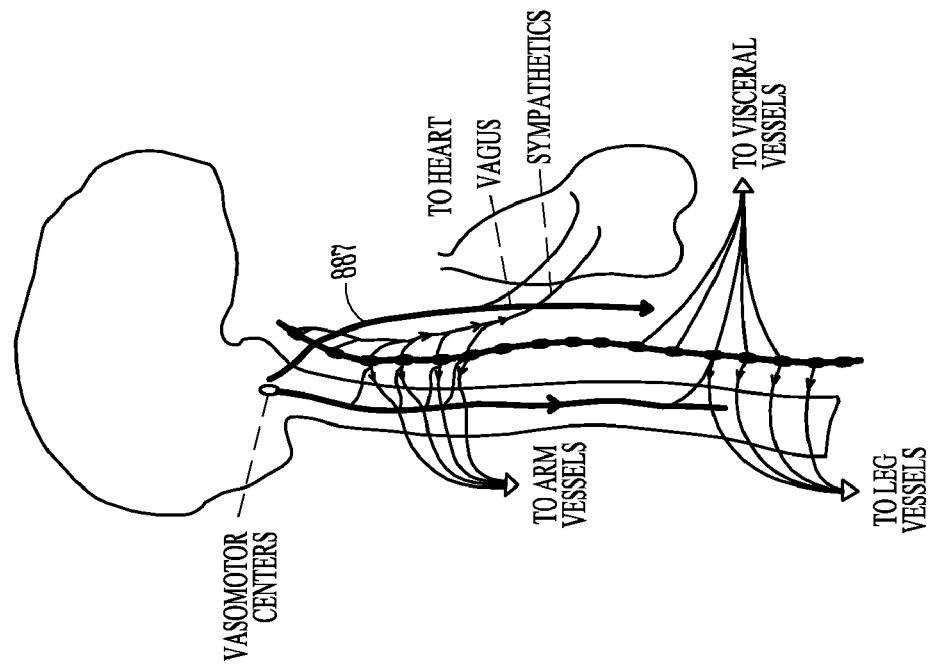
FIGS. 8C and 8D show neural pathways targeted by the present system, according to various embodiments.
Figure 8C:
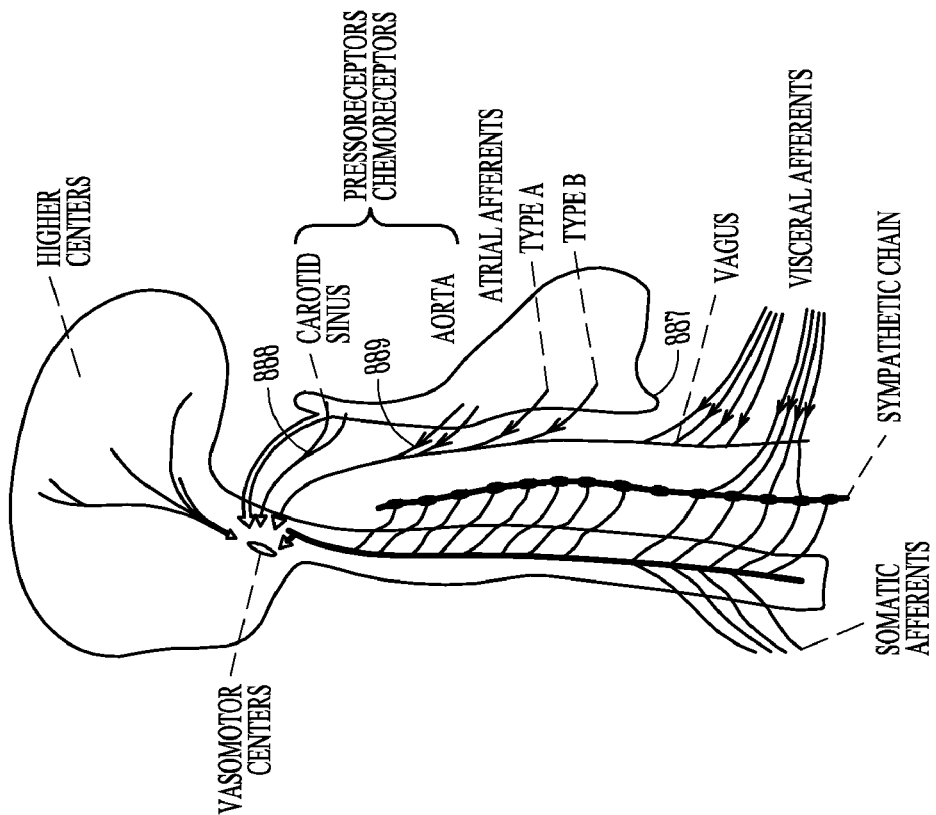

FIGS. 8C and 8D show neural pathways targeted by the present system, according to various embodiments. FIG. 8C generally illustrates afferent nerves to vasomotor centers. An afferent nerve conveys impulses toward a nerve center. A vasomotor center relates to nerves that dilate and constrict blood vessels to control the size of the blood vessels. FIG. 8D generally illustrates efferent nerves from vasomotor centers. An efferent nerve conveys impulses away from a nerve center. Afferent and efferent nerves can be stimulated transvascularly.

Figure 8E:
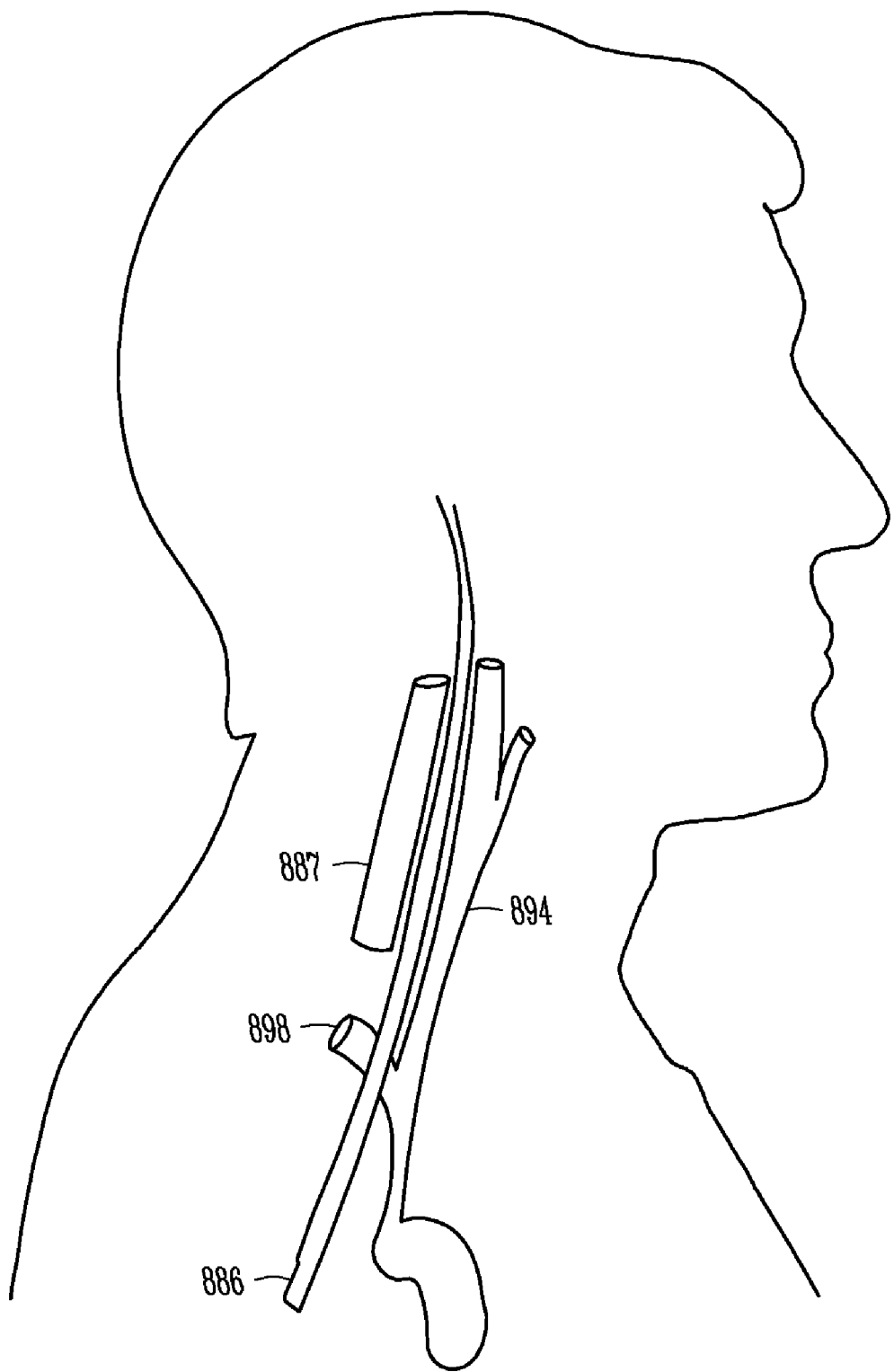
FIG. 8E is an illustration of an internal jugular vein near a vagus nerve for chronic implantation of the present apparatus, according to various embodiments.

FIG. 8E is an illustration of an internal jugular vein 887 near a vagus nerve 886 for chronic implantation of the present apparatus, according to various embodiments. In an example, the vagus nerve 886 is transvascularly stimulated from the internal jugular vein 887. A common carotid artery 894 and subclavian artery 898 are also shown in FIG. 8E. In other examples, nerve trunks innervating other organs, such as the lungs or kidneys are transvascularly stimulated. In an example, an expandable electrode such as a stent is implanted in a blood vessel proximate a nerve or nerve trunk that innervates the lungs or kidneys.

The vagus nerve includes a left and right vagus nerve. The right vagus nerve passes anterior to the subclavian artery, breaks up into pulmonary plexus posterior to root of the right lung, refers and then breaks up into esophageal and cardiac plexuses. The left vagus nerve passes to the left of the aortic arch and posterior to the root of the left lung, giving pulmonary, esophageal and cardiac plexuses. The described lead(s) provide minimally-invasive means to provide vagal stimulation, including selective vagal activation. Vagal nerve stimulation (VNS) can be used with the following control measures: R-R interval; P-R interval; Q-T interval; systolic pressure; diastolic pressure; MAP; stroke volume; respiratory rate; tidal volume; temperature; activity level; EEG; EMG; wake/sleep state; apnea/hypopnea Index; ENG; and EOG. Those of skill in the art will recognize that other control measures can be associated with VNS using the disclosed system.

While the above description discusses utilization of the present system adjacent the vagal nerve, the system can be used anywhere in a human body where a major vessel is running next to a nerve. Examples include but are not limited to the femoral nerve and the ulna/median nerve. In one embodiment, the vessel and nerve bundle are within a common sheath. In addition, the system can be used to sense and measure vessel characteristics.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An electrical lead, comprising:
    a proximal portion configured to connect to an implantable medical device;
    an expandable portion configured to be chronically implanted in a blood vessel proximate a nerve trunk and configured to be expanded to asymmetrically expand the blood vessel against the nerve trunk to stabilize the lead in a fixed position within the vessel; and
    a sensor along the expandable portion of the lead.

2. The electrical lead of claim 1, further comprising:
    a plurality of electrodes along the expandable portion of the lead.

3. The electrical lead of claim 2, wherein an electrical signal is delivered from the implanted medical device to one of the plurality of electrodes to transvascularly deliver neural stimulation from the electrode to at least one nerve bundle of the nerve trunk.

4. The electrical lead of claim 1, wherein the sensor is adapted to sense electrical signals from the nerve trunk.

5. The electrical lead of claim 1, wherein the sensor is adapted to sense blood pressure of the vessel.

6. A method, comprising:
    asymmetrically expanding an expandable portion of an electrical lead, adapted to be chronically implanted in a blood vessel proximate a nerve trunk, to stabilize the lead in a fixed position within the vessel;
    reshaping the blood vessel by further asymmetrically expanding the expandable portion, to expand the blood vessel against the nerve trunk to reshape the nerve trunk to spread nerve bundles of the nerve trunk; and
    delivering an electrical signal from an implanted medical device to an electrode positioned at the expandable portion of the lead to transvascularly deliver neural stimulation from the electrode to at least one of the nerve bundles of the nerve trunk.

7. The method of claim 6, wherein reshaping the blood vessel includes reshaping the blood vessel to an elongated shape.

8. The method of claim 6, wherein reshaping the nerve trunk includes reshaping the nerve trunk into an elongated shape as the vessel expands against the nerve trunk.

9. The method of claim 6, wherein asymmetrically expanding the expandable portion includes expanding the expandable portion into an oval shape.

10. The method of claim 6, wherein asymmetrically expanding includes expanding asymmetrically along a radial axis of the vessel against an inner wall of the vessel.

11. The method of claim 10, wherein expanding asymmetrically along a radial axis of the vessel against an inner wall of the vessel includes expanding against an inner wall proximate the nerve trunk.

12. The method of claim 6, wherein delivering an electrical signal includes delivering neural stimulation to selectively activate axons within the nerve trunk.

13. A method, comprising:
    placing a transvascular reshaping lead within a blood vessel to position an electrode on the lead proximate a neural target, the neural target including a nerve bundle within a nerve trunk;
    spreading nerve bundles within the nerve trunk by expanding the transvascular reshaping lead to asymmetrically expand the blood vessel against the nerve trunk;
    delivering an electrical signal from an implanted medical device attached to the lead to the electrode to transvascularly deliver neural stimulation from the electrode to the neural target.

14. The method of claim 13, wherein spreading nerve bundles within the nerve trunk by expanding the transvascular reshaping lead includes bringing vagal neural fibers of interest closer to the electrode.

15. The method of claim 13, wherein spreading nerve bundles within the nerve trunk by expanding the transvascular reshaping lead includes reducing a threshold bias for stimulating the neural target.

16. The method of claim 13, wherein the transvascular reshaping lead includes a transvascular prosthetic device.

17. The method of claim 13, further comprising:
sensing a parameter indicative of blood flow using a sensor positioned on the lead.

18. The method of claim 17, further comprising:
delivering neural stimulation in a closed loop system using the sensed parameter as feedback in the closed loop system.

19. The method of claim 13, further comprising:
sensing electrical signals from the nerve trunk using a sensor positioned on the lead.

20. The method of claim 19, further comprising:
delivering neural stimulation in a closed loop system using the sensed electrical signals as feedback in the closed loop system.

* * * * *